US006566390B2

(12) United States Patent
Petry et al.

(10) Patent No.: US 6,566,390 B2
(45) Date of Patent: May 20, 2003

(54) SUBSTITUTED AND UNSUBSTITUTED BENZOOXATHIAZOLES AND COMPOUNDS DERIVED THEREFROM

(75) Inventors: Stefan Petry, Frankfurt (DE); Karl-Heinz Baringhaus, Woelfersheim (DE); Swen Hoelder, Frankfurt am Main (DE); Guenter Mueller, Sulzbach (DE)

(73) Assignee: Aventis Pharma Deutschland GmbH (DE)

(*) Notice: Subject to any disclaimer, the term of this patent is extended or adjusted under 35 U.S.C. 154(b) by 0 days.

(21) Appl. No.: 09/925,019

(22) Filed: Aug. 9, 2001

(65) Prior Publication Data

US 2002/0055523 A1 May 9, 2002

(30) Foreign Application Priority Data

Aug. 9, 2000 (DE) .......................................... 100 38 709

(51) Int. Cl.⁷ .............................................. A61K 31/38
(52) U.S. Cl. ......................................... 514/443; 549/97
(58) Field of Search ........................... 568/28, 30, 31, 568/32, 33, 34, 35; 549/29, 41, 49, 51, 58; 514/430, 443, 446

(56) References Cited

U.S. PATENT DOCUMENTS 5,789,436 A * 8/1998 Kato et al. .................. 514/443

FOREIGN PATENT DOCUMENTS

| JP | 7-325942 | 12/1995 |
|----|----------|---------|
| WO | WO 92/05164 | 4/1992 |
| WO | WO 97/03974 | 2/1997 |
| WO | WO 98/32438 A1 | 7/1998 |
| WO | WO 98/32439 A1 | 7/1998 |
| WO | WO 99/11264 A1 | 3/1999 |
| WO | WO 99/36069 A1 | 7/1999 |
| WO | WO 00/05216 A1 | 3/2000 |

OTHER PUBLICATIONS

CA:99:194585 abs of Synth Commun by Levy 13(8) pp 639–48 1983.*
CA:69:51858 abs of Justus Liebigs Ann Chem by Horner et al 714 pp 91–111 1968.*
CA:82:43118 abs of Dokl Akad Nauk Tadzh. SSR by Nasyrov et al 17(6) pp 28–9 1974.*
CA:80:82552 abs of Dokl Akad Nauk Tadzh SSR by Ibragimov et al 16(10) pp 27–28 1973.*
CA:77:139695 abs of Dokl. Akad. Nauk. Tadzh. SSR by Ibragimov et al 15(4) pp 26–7 1972.*
CA:94:121179 abs of Helv Chim Acta by Oppolzer et al 63(6) pp 1703–5 1980.*
CA:87:84750 abs of Inst Khim Dushanbe Ussr by Ibragimov et al 20(3) pp 32–3 1977.*
CA:86:154751 abs of Aust J Chem by Adcock et al 29(12) pp 257–81 1976.*
CA:84:89930 abs of Khim Tadzh. Editor Solozhenkin by Nasyrov et al pp 107–110 1973.*
CA:117:69687 abs of J Chem Soc Chem Commun. by Kanematsu et al (10) pp 735–6 1992.*
CA:110:7815 abs of J Chem Soc Perkin Trans 1 by Grigg et al (6) pp 1357–64 1988.*
CA:97:181456 abs of Journal of the American Chem. Soc. by Hogeveen H 104(18) pp 4889–95 1982.*
CA:69:51858 abs of Justus Liebigs Annalen der Chemie by Horner et al 714 pp 91–111 1968.*
CA:87:84750 abs of Doklady Akademii Nauk Tadzhikskoi SSR by Ibragimov et al 20(3) pp 32–3 1977.*
CA:129:156955 abs of WO9832438 Jul. 1998.*
CA:124:2322030 abs of Fullerene Sci Technol. by Walter et al 4(1) pp 101–13 1996.*
CA;:107:217529 abs J Heterocycl. Chem by Chiarino et al 23(6) pp 1645–9 1986.*
CA:124:232492 abs WO 9533746 Dec. 1995.*
CA:95:143833 abs of J Med Chem 24 (11) pp 1300–4 by Acheson et al.*
CA:117:131207 abs of WO 9205164 Apr. 1992.*
CA:117:191879 abs of JP04128276 Apr. 1992.*
Peter A. Lanzetta et al. "An Improved Assay for Nanomole Amounts of Inorganic Phosphate", Analytical Biochemistry, 1979, 100, pp. 95–97.
Praveen Tyle "Iontophoretic Devices for Drug Delivery", Pharmaceutical Research, 1986, vol. 3, No. 6, p. 318.
Nicholas K. Tonks et al. "Characterization of the Major Protein–tyrosine–phosphatases of Human Placenta", The Journal of Biological Chemistry, May 15, 1988, vol. 263, No. 14, pp. 6731–6737.
Kenneth K. Andersen et al. "Acidity of Cyclic Sulfamates: Study of Substituted 1,2,3–Benzoxathiazole 2,2–Dioxides and Theoretical Investigation of the Effect of Conformation on Acidity", J. Org. Chem., 1995, 60, pp. 2003–2007.
Terrence R. Burke et al. "Small Molecule Interactions with Protein–Tyrosine Phosphatase PTP1B and Their Use in Inhibitor Design", Biochemsitry, 1996, 35, pp. 15989–15996.
Wanda A. Cromlish et al. "Selective Inhibition of Cyclooxygenase–1 and –2 Using Intact Insect Cell Assays", Biochemical Pharmacology, 1996, vol. 52, pp. 1777–1785.
Kenneth K. Andersen et al. "Reactivity of Nucleophiles Towards X–3–(p–Tolylsulfonyl)–1,2,3–Benzoxathiazole 2,2–Dioxides: Kinetics, Activation Volumes and Mechanism", Journal of Physical Organic Chemistry, 1997, vol. 10, pp. 175–181.

(List continued on next page.)

Primary Examiner—Jean F. Vollano
(74) Attorney, Agent, or Firm—Heller Ehrman White & McAuliffe, LLP

(57) ABSTRACT

The invention relates to substituted and unsubstituted 3H-benzo[1,2,3]oxathiazole 2,2-dioxides, 1,3-dihydrobenzo[1,2,5]thiadiazole 2,2-dioxides and 1,3-dihydro-benzo[c] isothiazole 2,2-dioxides, to their preparation and to their use in medicaments.

3 Claims, No Drawings

OTHER PUBLICATIONS

Beilstein Institut zur Förderung der Chyemischen Wissenschaften, Frankfurt am Main, DE; retrieved from Beilstein Xfire, accession No. 4387065, Zusammenfassung, Zusammenfassung, Journal of Heterocyclic Chemistry, Nr. 23, 1986, Seiten 1645–1649.

Beilstein Institut zur Förderung der Chyemischen Wissenschaften, Frankfurt am Main, DE; retrieved from Beilstein Xfire, accession No. 4800778, Zusammenfassung, Journal of Organic Chemistry, Bd. 56, Nr. 23, 1991, Seiten 6508–6516.

Beilstein Institut zur Förderung der Chyemischen Wissenschaften, Frankfurt am Main, DE; retrieved from Beilstein Xfire, accession No. 608462, Zusammenfassung, Journal of the Chemical Soc. C., 1971, Seiten 993–999.

Beilstein Institut zur Förderung der Chyemischen Wissenschaften, Frankfurt am Main, DE; retrived from Beilstein Xfire, accession No. 2047037, Zusammenfassung, C.R. Herd. Seances Acad. Sci., Nr. 203, 1936 Seite 194.

Beilstein Institut zur Förderung der Chyemischen Wissenschaften, Frankfurt am Main, DE; retrieved from Beilstein Xfire, accession No. 117793, Journal of American Chem. Soc., Nr. 81, 1959, Seite 4266.

Beilstein Institut zur Förderung der Chyemischen Wissenschaften, Frankfurt am Main, DE; retrieved from Beilstein Xfire, accession No. 4407, Chemische Berichte, Nr. 31, 1898 Seite 1857.

* cited by examiner

SUBSTITUTED AND UNSUBSTITUTED BENZOOXATHIAZOLES AND COMPOUNDS DERIVED THEREFROM

This application claims priority to German Patent Application 10038709.8-44, filed Aug. 9, 2000, which is hereby incorporated by reference, in its entirety.

BACKGROUND OF THE INVENTION

1. Field of the Invention

The present invention relates to substituted and unsubstituted 3H-benzo-[1,2,3]oxathiazole 2,2-dioxides, 1,3-dihydrobenzo[1,2,5]thiadiazole 2,2-dioxides and 1,3-dihydrobenzo[c]isothiazole 2,2-dioxides, to their preparation and to their use in medicaments.

2. Description of the Related Art

Aminobenzosultam derivatives acting as lipoxygenase inhibitors are known (WO 92/05164). Also known is the use of corresponding bifunctional derivatives as charge transporters in photoreceptors (JP 95/325942). Andersen et al. described the synthesis of toluenesulfonyl-protected derivatives and studies of reactions of these derivatives with nucleophiles (K. Andersen et al., J. Phys. Org. Chem., 10, 175–181 (1997); K. Andersen et al., J Org. Chem., 60, 2003–2007 (1995)).

SUMMARY OF THE INVENTION

It was an object of the present invention to provide novel substituted and unsubstituted benzooxathiazoles and their preparation and use as pharmaceutically active compounds. In particular, it was an object to provide novel substituted and unsubstituted benzooxathiazoles for treating type 1 and type 2 diabetes, insulin resistance and pathological obesity.

The present invention relates to compounds of the formula I

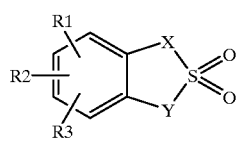

I in which
X is $CH_2$, O, N;
Y is $CH_2$, O, N;
R1, R2, R3 are each independently of one another
H, F, Cl, Br, I, $NH_2$, OH, $NO_2$, COOH;
$COO(C_1-C_6)$alkyl, $CONH_2$, $CONH(C_1-C_{16})$alkyl, $CONH(C_1-C_{16})$alkenyl, $CONH(C_1-C_6)$alkyl-phenyl, where phenyl may be mono- to trisubstituted by $O-(C_1-C_{10})$alkyl or $O-(C_1-C_{10})$alkyl-phenyl, $CONH(C_1-C_6)$alkyl-benzimidazole, where the benzimidazole ring may be mono- to trisubstituted by S-phenyl, wherein the S-phenyl may be mono- to trisubstituted by F, Cl, Br, I, OH, $CF_3$, $NO_2$, CN, $OCF_3$, $O-(C_1-C_{10})$alkyl, $NH_2$, $NH(C_1-C_6)$alkyl, COOH, $COO(C_1-C_6)$alkyl,
$CONH_2$;
$O-(C_1-C_6)$alkyl;
$(C_1-C_6)$alkyl, $(C_2-C_6)$alkenyl, $(C_2-C_6)$alkynyl, $(C_1-C_6)$alkyl-COOH, $(C_1-C_6)$alkyl-aryl, where aryl may be phenyl, naphthyl, biphenyl, thienyl or pyridyl and the aryl moiety may in each case be mono- to trisubstituted by F, Cl, Br, I, OH, $CF_3$, $NO_2$, CN, $OCF_3$, $O-(C_1-C_{10})$alkyl, $NH_2$, $NH(C_1-C_6)$alkyl, COOH, $COO(C_1-C_6)$alkyl,
$CONH_2$;
Phenyl, biphenyl, 1-or 2-naphthyl, 2-,3-or 4-pyridyl, 2-or 3-furanyl or 2-or 3-thienyl, where the phenyl, biphenyl, naphthyl, pyridyl, furanyl or thienyl rings may in each case be mono- to trisubstituted by F, Cl, Br, I, OH, $CF_3$, $NO_2$, CN, $OCF_3$, $O-(C_1-C_{10})$alkyl, $NH_2$, $NH(C_1-C_6)$alkyl, COOH, $COO(C_1-C_6)$alkyl, $CONH_2$; $(C_3-C_{18})$cycloalkyl, where in the alkyl radicals one or more hydrogens may be replaced by fluorine or one hydrogen may be replaced by OH, $(C_1-C_6)$alkyl-phenyl or $O-(C_1-C_6)$alkyl-phenyl,
NCO, $NSO_3-(C_1-C_{10})$alkyl; or in each case two of the radicals R1 and R2 or R2 and R3 or R1 and R3 together form a fused aryl radical, where aryl may be phenyl, naphthyl, biphenyl, thienyl or pyridyl and the aryl moiety may in each case be mono- to trisubstituted by F, Cl, Br, I, OH, $CF_3$, $NO_2$, CN, $OCF_3$, $O-(C_1-C_{10})$alkyl, $NH_2$, $NH(C_1-C_6)$alkyl, COOH, $COO(C_1-C_6)$alkyl, $CONH_2$;

or its physiologically acceptable salts or prodrugs.

The invention preferably relates to compounds of the formula I wherein
X is O, N;
Y is O, N;
R1 is H, F, Cl, Br, I, $NH_2$, OH, $NO_2$, COOH;
$COO(C_1-C_6)$alkyl, $CONH_2$, $CONH(C_1-C_6)$alkyl, $CONH(C_1-C_6)$alkenyl, $CONH(C_1-C_6)$alkyl-phenyl, where phenyl may be mono- to trisubstituted by $O-(C_1-C_{10})$alkyl or $O-(C_1-C_{10})$alkyl-phenyl, $CONH(C_1-C_6)$alkyl-benzimidazole, where the benzimidazole ring may be mono- to trisubstituted by S-phenyl, wherein the S-phenyl may be mono- to trisubstituted by F, Cl, Br, I, OH, $CF_3$, $NO_2$, CN, $OCF_3$, $O-(C_1-C_{10})$alkyl, $NH_2$, $NH(C_1-C_6)$alkyl, COOH, $COO(C_1-C_6)$alkyl,
$CONH_2$;
$O-(C_1-C_6)$alkyl;
$(C_1-C_6)$alkyl, $(C_2-C_6)$alkenyl, $(C_2-C_6)$alkynyl, $(C_1-C_6)$alkyl-COOH, $(C_1-C_6)$alkyl-aryl, where aryl may be phenyl, naphthyl, biphenyl, thienyl or pyridyl and the aryl moiety may in each case be mono- to trisubstituted by F, Cl, Br, I, OH, $CF_3$, $NO_2$, CN, $OCF_3$, $O-(C_1-C_{10})$alkyl, $NH_2$, $NH(C_1-C_6)$alkyl, COOH, $COO(C_1-C_6)$alkyl,
$CONH_2$;
Phenyl, biphenyl, 1-or 2-naphthyl, 2-, 3-or 4-pyridyl, 2-or 3-furanyl or 2-or 3-thienyl, where the phenyl, biphenyl, naphthyl, pyridyl, furanyl or thienyl rings may in each case be mono- to trisubstituted by F, Cl, Br, I, OH, $CF_3$, $NO_2$, CN, $OCF_3$, $O-(C_1-C_{10})$alkyl, $NH_2$, $NH(C_1-C_6)$alkyl, COOH, $COO(C_1-C_6)$alkyl, $CONH_2$; $(C_3-C_{18})$cycloalkyl, where in the alkyl radicals one or more hydrogens may be replaced by fluorine or one hydrogen may be replaced by OH, $(C_1-C_6)$alkyl-phenyl or $O-(C_1-C_6)$alkyl-phenyl,
NCO, $NSO_3-(C_1-C_{10})$alkyl;
R2 is H, F, Cl, Br, I, $NH_2$, OH, $NO_2$, COOH;
$COO(C_1-C_6)$alkyl, $CONH_2$, $CONH(C_1-C_{16})$alkyl, $CONH(C_1-C_{16})$alkenyl, $CONH(C_1-C_6)$alkyl-phenyl, where phenyl may be mono- to trisubstituted by $O-(C_1-C_{10})$alkyl or $O-(C_1-C_{10})$alkyl-phenyl, $CONH(C_1-C_6)$alkyl-benzimidazole, where the benzimidazole ring may be mono- to trisubstituted by S-phenyl, wherein the S-phenyl may be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$;

O-($C_1$–$C_6$)alkyl;

($C_1$–$C_6$)alkyl, ($C_2$–$C_6$)alkenyl, ($C_2$–$C_6$)alkynyl, ($C_1$–$C_6$)alkyl-COOH, ($C_1$–$C_6$)alkyl-aryl, where aryl may be phenyl, naphthyl, biphenyl, thienyl or pyridyl and the aryl moiety may in each case be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$;

Phenyl, biphenyl, 1-or 2-naphthyl, 2-, 3-or 4-pyridyl, 2-or 3-furanyl or 2-or 3-thienyl, where the phenyl, biphenyl, naphthyl, pyridyl, furanyl or thienyl rings may in each case be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$; ($C_3$–$C_{18}$)cycloalkyl, where in the alkyl radicals one or more hydrogens may be replaced by fluorine or one hydrogen may be replaced by OH, ($C_1$–$C_6$)alkyl-phenyl or O-($C_1$–$C_6$)alkyl-phenyl, NCO, $NSO_3$-($C_1$–$C_{10}$)alkyl;

R3 is H, F, Cl, Br, I, $NH_2$, OH, $NO_2$, COOH;

COO($C_1$–$C_6$)alkyl, $CONH_2$, CONH($C_1$–$C_{16}$)alkyl, CONH($C_1$–$C_{16}$)alkenyl, CONH($C_1$–$C_6$)alkyl-phenyl, where phenyl may be mono- to trisubstituted by O-($C_1$–$C_{10}$)alkyl or O-($C_1$–$C_{10}$)alkyl-phenyl, CONH($C_1$–$C_6$)alkyl-benzimidazole, where the benzimidazole ring may be mono- to trisubstituted by S-phenyl, wherein the S-phenyl may be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$;

O-($C_1$–$C_6$)alkyl;

($C_1$–$C_6$)alkyl, ($C_2$–$C_6$)alkenyl, ($C_2$–$C_6$)alkynyl, ($C_1$–$C_6$)alkyl-COOH, ($C_1$–$C_6$)alkyl-aryl, where aryl may be phenyl, naphthyl, biphenyl, thienyl or pyridyl and the aryl moiety may in each case be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$;

Phenyl, biphenyl, 1-or 2-naphthyl, 2-, 3-or 4-pyridyl, 2-or 3-furanyl or 2-or 3-thienyl, where the phenyl, biphenyl, naphthyl, pyridyl, furanyl or thienyl rings may in each case be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$; ($C_3$–$C_{18}$)cycloalkyl, where in the alkyl radicals one or more hydrogens may be replaced by fluorine or one hydrogen may be replaced by OH, ($C_1$–$C_6$)alkyl-phenyl or O-($C_1$–$C_6$)alkyl-phenyl, NCO, $NSO_3$-($C_1$–$C_{10}$)alkyl;

or its physiologically acceptable salts or prodrugs.

The invention furthermore preferably relates to compounds of the formula I wherein X is O, N;

Y is N;

R1 is H, F, Cl, Br, I, $NH_2$, OH, $NO_2$, COOH;

COO($C_1$–$C_6$)alkyl, $CONH_2$, CONH($C_1$–$C_{16}$)alkyl, CONH($C_1$–$C_{16}$)alkenyl, CONH($C_1$–$C_6$)alkyl-phenyl, where phenyl may be mono- to trisubstituted by O-($C_1$–$C_{10}$)alkyl or O-($C_1$–$C_{10}$)alkyl-phenyl, CONH($C_1$–$C_6$)alkyl-benzimidazole, where the benzimidazole ring may be mono- to trisubstituted by S-phenyl, wherein the S-phenyl may be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$;

O-($C_1$–$C_6$)alkyl;

($C_1$–$C_6$)alkyl, ($C_2$–$C_6$)alkenyl, ($C_2$–$C_6$)alkynyl, ($C_1$–$C_6$)alkyl-COOH, ($C_1$–$C_6$)alkyl-aryl, where aryl may be phenyl, naphthyl, biphenyl, thienyl or pyridyl and the aryl moiety may in each case be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$;

Phenyl, biphenyl, 1-or 2-naphthyl, 2-, 3-or 4-pyridyl, 2-or 3-furanyl or 2-or 3-thienyl, where the phenyl, biphenyl, naphthyl, pyridyl, furanyl or thienyl rings may in each case be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$; ($C_3$–$C_{18}$)cycloalkyl, where in the alkyl radicals one or more hydrogens may be replaced by fluorine or one hydrogen may be replaced by OH, ($C_1$–$C_6$)alkyl-phenyl or O-($C_1$–$C_6$)alkyl-phenyl, NCO, $NSO_3$-($C_1$–$C_{10}$)alkyl;

R2 is H, F, Cl, Br, I, $NH_2$, OH, $NO_2$, COOH;

COO($C_1$–$C_6$)alkyl, $CONH_2$, CONH($C_1$–$C_{16}$)alkyl, CONH($C_1$–$C_{16}$)alkenyl, CONH($C_1$–$C_6$)alkyl-phenyl, where phenyl may be mono- to trisubstituted by O-($C_1$–$C_{10}$)alkyl or O-($C_1$–$C_{10}$)alkyl-phenyl, CONH($C_1$–$C_6$)alkyl-benzimidazole, where the benzimidazole ring may be mono- to trisubstituted by S-phenyl, wherein the S-phenyl may be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$;

O-($C_1$–$C_6$)alkyl;

($C_1$–$C_6$)alkyl, ($C_2$–$C_6$)alkenyl, ($C_2$–$C_6$)alkynyl, ($C_1$–$C_6$)alkyl-COOH, ($C_1$–$C_6$)alkyl-aryl, where aryl may be phenyl, naphthyl, biphenyl, thienyl or pyridyl and the aryl moiety may in each case be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$;

Phenyl, biphenyl, 1-or 2-naphthyl, 2-, 3-or 4-pyridyl, 2-or 3-furanyl or 2-or 3-thienyl, where the phenyl, biphenyl, naphthyl, pyridyl, furanyl or thienyl rings may in each case be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$; ($C_3$–$C_{18}$)cycloalkyl, where in the alkyl radicals one or more hydrogens may be replaced by fluorine or one hydrogen may be replaced by OH, ($C_1$–$C_6$)alkyl-phenyl or O-($C_1$–$C_6$)alkyl-phenyl, NCO, $NSO_3$-($C_1$–$C_{10}$)alkyl;

R3 is COO($C_1$–$C_6$)alkyl, $CONH_2$, CONH($C_1$–$C_{16}$)alkyl, CONH($C_1$–$C_{16}$)alkenyl, CONH($C_1$–$C_6$)alkyl-phenyl, where phenyl may be mono- to trisubstituted by O-($C_1$–$C_{10}$)alkyl or O-($C_1$–$C_{10}$)alkyl-phenyl, CONH($C_1$–$C_6$)alkyl-benzimidazole, where the benzimidazole ring may be mono- to trisubstituted by S-phenyl, wherein the S-phenyl may be mono- to trisubstituted by F, Cl, Br, I, OH, $CF_3$, $NO_2$, CN, $OCF_3$, $O$-$(C_1$-$C_{10})$alkyl, $NH_2$, $NH(C_1$-$C_6)$alkyl, COOH, $COO(C_1$-$C_6)$alkyl, $CONH_2$;

$O$-$(C_1$-$C_6)$alkyl;

$(C_1$-$C_6)$alkyl, $(C_2$-$C_6)$alkenyl, $(C_2$-$C_6)$alkynyl, $(C_1$-$C_6)$alkyl-COOH, $(C_1$-$C_6)$alkyl-aryl, where aryl may be phenyl, naphthyl, biphenyl, thienyl or pyridyl and the aryl moiety may in each case be mono- to trisubstituted by F, Cl, Br, I, OH, $CF_3$, $NO_2$, CN, $OCF_3$, $O$-$(C_1$-$C_{10})$alkyl, $NH_2$, $NH(C_1$-$C_6)$alkyl, COOH, $COO(C_1$-$C_6)$alkyl, $CONH_2$;

Phenyl, biphenyl, 1-or 2-naphthyl, 2-, 3-or 4-pyridyl, 2-or 3-furanyl or 2-or 3-thienyl, where the phenyl, biphenyl, naphthyl, pyridyl, furanyl or thienyl rings may in each case be mono- to trisubstituted by F, Cl, Br, I, OH, $CF_3$, $NO_2$, CN, $OCF_3$, $O$-$(C_1$-$C_{10})$alkyl, $NH_2$, $NH(C_1$-$C_6)$alkyl, COOH, $COO(C_1$-$C_6)$alkyl, $CONH_2$; $(C_3$-$C_{18})$cycloalkyl, where in the alkyl radicals one or more hydrogens may be replaced by fluorine or one hydrogen may be replaced by OH, $(C_1$-$C_6)$alkyl-phenyl or $O$-$(C_1$-$C_6)$alkyl-phenyl, NCO, $NSO_3$-$(C_1$-$C_{10})$alkyl;

or its physiologically acceptable salts or prodrugs.

The invention furthermore preferably relates to compounds of the formula I wherein X is O;

Y is N;

R1 is H, F, Cl, Br, I, $NH_2$, OH, $NO_2$, COOH;

$COO(C_1$-$C_6)$alkyl, $CONH_2$, $CONH(C_1$-$C_{16})$alkyl, $CONH(C_1$-$C_{16})$alkenyl, $CONH(C_1$-$C_6)$alkyl-phenyl, where phenyl may be mono- to trisubstituted by $O$-$(C_1$-$C_{10})$alkyl or $O$-$(C_1$-$C_{10})$alkyl-phenyl, CONH $(C_1$-$C_6)$alkyl-benzimidazole, where the benzimidazole ring may be mono- to trisubstituted by S-phenyl, wherein the S-phenyl may be mono- to trisubstituted by F, Cl, Br, I, OH, $CF_3$, $NO_2$, CN, $OCF_3$, $O$-$(C_1$-$C_{10})$alkyl, $NH_2$, $NH(C_1$-$C_6)$alkyl, COOH, $COO(C_1$-$C_6)$alkyl, $CONH_2$;

$O$-$(C_1$-$C_6)$alkyl;

$(C_1$-$C_6)$alkyl, $(C_2$-$C_6)$alkenyl, $(C_2$-$C_6)$alkynyl, $(C_1$-$C_6)$alkyl-COOH, $(C_1$-$C_6)$alkyl-aryl, where aryl may be phenyl, naphthyl, biphenyl, thienyl or pyridyl and the aryl moiety may in each case be mono- to trisubstituted by F, Cl, Br, I, OH, $CF_3$, $NO_2$, CN, $OCF_3$, $O$-$(C_1$-$C_{10})$alkyl, $NH_2$, $NH(C_1$-$C_6)$alkyl, COOH, $COO(C_1$-$C_6)$alkyl, $CONH_2$;

Phenyl, biphenyl, 1-or 2-naphthyl, 2-, 3-or 4-pyridyl, 2-or 3-furanyl or 2-or 3-thienyl, where the phenyl, biphenyl, naphthyl, pyridyl, furanyl or thienyl rings may in each case be mono- to trisubstituted by F, Cl, Br, I, OH, $CF_3$, $NO_2$, CN, $OCF_3$, $O$-$(C_1$-$C_{10})$alkyl, $NH_2$, $NH(C_1$-$C_6)$alkyl, COOH, $COO(C_1$-$C_6)$alkyl, $CONH_2$; $(C_3$-$C_{18})$cycloalkyl, where in the alkyl radicals one or more hydrogens may be replaced by fluorine or one hydrogen may be replaced by OH, $(C_1$-$C_6)$alkyl-phenyl or $O$-$(C_1$-$C_6)$alkyl-phenyl, NCO, $NSO_3$-$(C_1$-$C_{10})$alkyl;

R2 is F, Cl, Br, I, $NH_2$, OH, $NO_2$, COOH;

$COO(C_1$-$C_6)$alkyl, $CONH_2$, $CONH(C_1$-$C_{16})$alkyl, $CONH(C_1$-$C_{16})$alkenyl, $CONH(C_1$-$C_6)$alkyl-phenyl, where phenyl may be mono- to trisubstituted by $O$-$(C_1$-$C_{10})$alkyl or $O$-$(C_1$-$C_{10})$alkyl-phenyl, CONH $(C_1$-$C_6)$alkyl-benzimidazole, where the benzimidazole ring may be mono- to trisubstituted by S-phenyl, wherein the S-phenyl may be mono- to trisubstituted by F, Cl, Br, I, OH, $CF_3$, $NO_2$, CN, $OCF_3$, $O$-$(C_1$-$C_{10})$alkyl, $NH_2$, $NH(C_1$-$C_6)$alkyl, COOH, $COO(C_1$-$C_6)$alkyl, $CONH_2$;

$O$-$(C_1$-$C_6)$alkyl;

$(C_1$-$C_6)$alkyl, $(C_2$-$C_6)$alkenyl, $(C_2$-$C_6)$alkynyl, $(C_1$-$C_6)$alkyl-COOH, $(C_1$-$C_6)$alkyl-aryl, where aryl may be phenyl, naphthyl, biphenyl, thienyl or pyridyl and the aryl moiety may in each case be mono- to trisubstituted by F, Cl, Br, I, OH, $CF_3$, $NO_2$, CN, $OCF_3$, $O$-$(C_1$-$C_{10})$alkyl, $NH_2$, $NH(C_1$-$C_6)$alkyl, COOH, $COO(C_1$-$C_6)$alkyl, $CONH_2$;

$(C_3$-$C_{18})$cycloalkyl, where in the alkyl radicals one or more hydrogens may be replaced by fluorine or one hydrogen may be replaced by OH, $(C_1$-$C_6)$alkyl-phenyl or $O$-$(C_1$-$C_6)$alkyl-phenyl, NCO, $NSO_3$-$(C_1$-$C_{10})$alkyl;

R3 is $COO(C_1$-$C_6)$alkyl, $CONH_2$, $CONH(C_1$-$C_{16})$alkyl, $CONH(C_1$-$C_{16})$alkenyl, $CONH(C_1$-$C_6)$alkyl-phenyl, where phenyl may be mono- to trisubstituted by $O$-$(C_1$-$C_{10})$alkyl or $O$-$(C_1$-$C_{10})$alkyl-phenyl, $CONH(C_1$-$C_6)$alkyl-benzimidazole, where the benzimidazole ring may be mono- to trisubstituted by S-phenyl, wherein the S-phenyl may be mono- to trisubstituted by F, Cl, Br, I, OH, $CF_3$, $NO_2$, CN, $OCF_3$, $O$-$(C_1$-$C_{10})$alkyl, $NH_2$, $NH(C_1$-$C_6)$alkyl, COOH, $COO(C_1$-$C_6)$alkyl, $CONH_2$;

$O$-$(C_1$-$C_6)$alkyl;

$(C_1$-$C_6)$alkyl, $(C_2$-$C_6)$alkenyl, $(C_2$-$C_6)$alkynyl, $(C_1$-$C_6)$alkyl-COOH, $(C_1$-$C_6)$alkyl-aryl, where aryl may be phenyl, naphthyl, biphenyl, thienyl or pyridyl and the aryl moiety may in each case be mono- to trisubstituted by F, Cl, Br, I, OH, $CF_3$, $NO_2$, CN, $OCF_3$, $O$-$(C_1$-$C_{10})$alkyl, $NH_2$, $NH(C_1$-$C_6)$alkyl, COOH, $COO(C_1$-$C_6)$alkyl, $CONH_2$;

Phenyl, biphenyl, 1-or 2-naphthyl, 2-, 3-or 4-pyridyl, 2-or 3-furanyl or 2-or 3-thienyl, where the phenyl, biphenyl, naphthyl, pyridyl, furanyl or thienyl rings may in each case be mono- to trisubstituted by F, Cl, Br, I, OH, $CF_3$, $NO_2$, CN, $OCF_3$, $O$-$(C_1$-$C_{10})$alkyl, $NH_2$, $NH(C_1$-$C_6)$alkyl, COOH, $COO(C_1$-$C_6)$alkyl, $CONH_2$; $(C_3$-$C_{18})$cycloalkyl, where in the alkyl radicals one or more hydrogens may be replaced by fluorine or one hydrogen may be replaced by OH, $(C_1$-$C_6)$alkyl-phenyl or $O$-$(C_1$-$C_6)$alkyl-phenyl, NCO, $NSO_3$-$(C_1$-$C_{10})$alkyl;

or its physiologically acceptable salts or prodrugs.

The invention further relates to a method of inhibiting a PTPase, preferentially PTP1B, CD45, LAR, SHP-1, SHP-2, PTPa or HePTP, comprising administering to a subject in need thereof an effective amount of one or more compounds of formula 1 as described above.

The invention further relates to a method of treating type 1 diabetes, type 2 diabetes, insuling resistance, or pathological obesity comprising administering to a subject in need thereof an effective amount of one or more compounds of formula 1 as described above.

The invention still further relates to a method of preparing a pharmaceutical composition comprising the steps of mixing one or more compounds of formula 1 with one or more pharmaceutically acceptable excipients and bringing this mixture into a form suitable for administration.

Other compounds, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF A PREFERRED EMBODIMENT

In a compound of the formula I, X and Y in preferred embodiments may in each case independently of one another be $CH_2$, O or N.

The invention relates to compounds of the formula I, in the form of their racemates, racemic mixtures and pure enantiomers, and to their diastereomers and mixtures thereof.

The alkyl, alkenyl and alkynyl radicals in the substituents R1, R2 and R3 can be either straight-chain or branched.

On account of their higher water solubility, pharmaceutically acceptable salts are particularly suitable for medicinal applications compared with the starting materials or base compounds. These salts must have a pharmaceutically acceptable anion or cation. Suitable pharmaceutically acceptable acid addition salts of the compounds according to the invention are salts of inorganic acids, such as hydrochloric acid, hydrobromic acid, phosphoric acid, metaphosphoric acid, nitric acid, sulfonic acid and sulfuric acid, and of organic acids, such as, for example, acetic acid, benzenesulfonic acid, benzoic acid, citric acid, ethanesulfonic acid, fumaric acid, gluconic acid, glycolic acid, isethionic acid, lactic acid, lactobionic acid, maleic acid, malic acid, methanesulfonic acid, succinic acid, p-toluenesulfonic acid, tartaric acid and trifluoroacetic acid. For medicinal purposes, the chlorine salt is particularly preferred. Suitable pharmaceutically acceptable basic salts are ammonium salts, alkali metal salts (such as sodium salts and potassium salts) and alkaline earth metal salts (such as magnesium salts and calcium salts).

Salts having a pharmaceutically acceptable anion are likewise included in the scope of the invention as useful intermediates for the production or purification of pharmaceutically acceptable salts and/or for use in nontherapeutic, for example in-vitro, applications.

Salts of chemical compounds of the formula I can be prepared using customary methods familiar to the person skilled in the art. A salt can be prepared, for example, by combining a chemical compound of the formula I with an inorganic or organic acid or base in a solvent or diluent.

The term "physiologically functional derivative" used here relates to any physiologically acceptable derivative of a compound of the formula I according to the invention, for example an ester, which on administration to a mammal, such as, for example, man, is able (directly or indirectly) to form a compound of the formula I or an active metabolite thereof.

The physiologically functional derivatives also include prodrugs of the compounds according to the invention. Such prodrugs can be metabolized in vivo to a compound according to the invention. These prodrugs can themselves be active or inactive.

The compounds according to the invention can also be present in various polymorphic forms, for example as amorphous and crystalline polymorphic forms. All polymorphic forms of the compounds according to the invention are included in the scope of the invention and are a further aspect of the invention.

Hereinbelow, all references to "compound(s) according to formula (I)" refer to a compound/compounds of the formula (I) as described above, and to their salts, solvates and physiologically functional derivatives as described herein.

The amount of a compound according to formula (I) which is necessary in order to achieve the desired biological effect is dependent on a number of factors, for example the specific compound selected, the intended use, the manner of administration and the clinical condition of the patient. In general, the daily dose is in the range from 0.3 mg to 100 mg (typically from 3 mg to 50 mg) per day per kilogram of bodyweight, for example 3–10 mg/kg/day. An intravenous dose can be, for example, in the range from 0.3 mg to 1.0 mg/kg, which can be suitably administered as an infusion of 10 ng to 100 ng per kilogram per minute. Suitable infusion solutions for these purposes can contain, for example, from 0.1 ng to 10 mg, typically from 1 ng to 10 mg per milliliter. Individual doses can contain, for example, from 1 mg to 10 g of the active compound. Thus, ampoules for injections can contain, for example, from 1 mg to 100 mg, and orally administrable individual dose formulations, such as, for example, tablets or capsules, can contain, for example, from 1.0 to 1000 mg, typically from 10 to 600 mg. In the case of pharmaceutically acceptable salts, the abovementioned weight details relate to the weight of the dihydrothiazolium ion derived from the salt. For the prophylaxis or therapy of the abovementioned conditions, the compounds according to formula (I) can be used themselves as the compound, but they are preferably present in the form of a pharmaceutical composition with a tolerable excipient. The excipient must of course be tolerable, in the sense that it is compatible with the other constituents of the composition and is not harmful to the patient's health. The excipient can be a solid or a liquid or both and is preferably formulated with the compound as an individual dose, for example as a tablet which can contain from 0.05% to 95% by weight of the active compound. Further pharmaceutically active substances can also be present, including further compounds according to formula (I). The pharmaceutical compositions according to the invention can be prepared by one of the known pharmaceutical methods, which essentially consist in mixing the constituents with pharmacologically acceptable excipients and/or auxiliaries.

Pharmaceutical compositions according to the invention are those which are suitable for oral, rectal, topical, peroral (e.g. sublingual) and parenteral (e.g. subcutaneous, intramuscular, intradermal or intravenous) administration, although the most suitable manner of administration in each individual case is dependent on the nature and severity of the condition to be treated and on the nature of the compound according to formula (I) used in each case. Sugar-coated formulations and sugar-coated delayed release formulations are also included in the scope of the invention. Acid-resistant and enteric formulations are preferred. Suitable enteric coatings include cellulose acetate phthalate, polyvinyl acetate phthalate, hydroxypropylmethylcellulose phthalate and anionic polymers of methacrylic acid and methyl methacrylate.

Suitable pharmaceutical compounds for oral administration can be present in separate units, such as, for example, capsules, cachets, lozenges or tablets which in each case contain a certain amount of the compound according to formula (I); as powders or granules; as solution or suspension in an aqueous or nonaqueous liquid; or as an oil-in-water or water-in-oil emulsion. As already mentioned, these compositions can be prepared by any suitable pharmaceutical method which includes a step in which the active compound and the excipient (which can consist of one or more additional constituents) are brought into contact. In general, the compositions are prepared by uniform and homogeneous mixing of the active compound with a liquid and/or finely divided solid excipient, after which the product is shaped, if necessary. Thus a tablet, for example, can be prepared by pressing or shaping a powder or granules of the compound, if appropriate with one or more additional constituents. Pressed tablets can be prepared by tableting the compound in free-flowing form, such as, for example, in a powder or granules, if appropriate mixed with a binder, lubricant, inert diluent and/or one (a number of) surface-active/dispersing agent(s) in a suitable machine. Shaped tablets can be prepared by shaping the pulverulent compound, moistened with an inert liquid diluent, in a suitable machine.

Pharmaceutical compositions which are suitable for per-oral (sublingual) administration include lozenges which contain a compound according to formula (I) with a flavoring, customarily sucrose and gum arabic or tragacanth, and pastilles which include the compound in an inert base such as gelatin and glycerol or sucrose and gum arabic.

Suitable pharmaceutical compositions for parenteral administration preferably include sterile aqueous preparations of a compound according to formula (I), which are preferably isotonic with the blood of the intended recipient. These preparations are preferably administered intravenously, although the administration can also take place subcutaneously, intramuscularly or intradermally as an injection. These preparations can preferably be prepared by mixing the compound with water and rendering the obtained solution sterile and isotonic with the blood. Injectable compositions according to the invention in general contain from 0.1 to 5% by weight of the active compound.

Suitable pharmaceutical compositions for rectal administration are preferably present as individual dose suppositories. These can be prepared by mixing a compound according to formula (I) with one or more conventional solid excipients, for example cocoa butter, and shaping the resulting mixture.

Suitable pharmaceutical compositions for topical application to the skin are preferably present as ointment, cream, lotion, paste, spray, aerosol or oil. Excipients which can be used are petroleum jelly, lanolin, polyethylene glycols, alcohols and combinations of two or more of these substances. The active compound is in general present in a concentration of from 0.1 to 15%, for example of from 0.5 to 2%, by weight of the composition.

Transdermal administration is also possible. Suitable pharmaceutical compositions for transdermal administration can be present as individual patches which are suitable for long-term close contact with the epidermis of the patient. Such patches suitably contain the active compound in an optionally buffered aqueous solution, dissolved and/or dispersed in an adhesive or dispersed in a polymer. A suitable active compound concentration is from about 1% to 35%, preferably from about 3% to 15%. As a particular possibility, the active compound can be released by electrotransport or iontophoresis, as described, for example, in Pharmaceutical Research, 2(6):318 (1986).

The invention furthermore relates to a process for preparing the compounds of the formula I, which comprises obtaining the compounds of the formula I in such a way that the procedure is according to the following reaction scheme:

A benzylidenediamine of the formula II in which R1, R2 and R3 are as defined in the sections above is reacted with sulfonediamine. In particular, it is possible to prepare a chemical compound of the formula I in which X is N and Y is N in this manner.

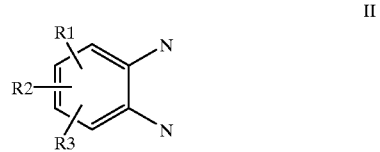

II

It is also possible to prepare a compound of the present invention by reacting a 2-aminophenol of the formula III whose N group is protected and whose substituents R1, R2 and R3 are as defined under formula I with sulfuryl chloride, followed by removal of the protective group. The N group of the 2-aminophenol of the formula III is preferably protected by p-toluenesulfonyl.

Alternatively, a 2-aminophenol of the formula III in which the 2-aminophenol is present without protective group is used as starting material. This 2-aminophenol of the formula III whose N group is not protected and whose substituents R1, R2 and R3 are each defined as in claim 1 is treated with sulfonyldiimidazole under basic conditions. The base used can, for example, be triethylamine, a Hünig base or DBU (1,5-diazabicyclo[4.3.0]non-5-ene).

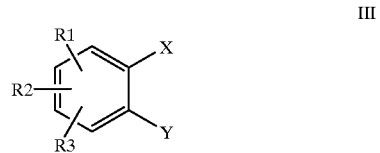

III

It is also possible to prepare a compound of the present invention by a process in which initially a 1-bromomethyl-2-nitrobenzene of the formula IV

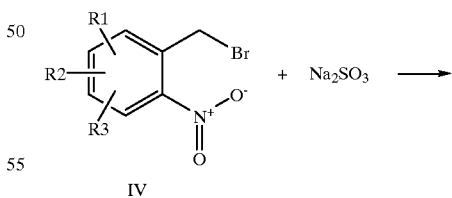

IV

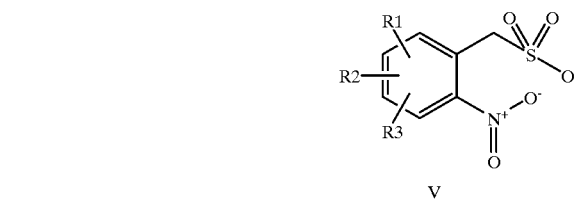

V whose substituents R1, R2 and R3 are as defined under formula I with Na$_2$SO$_3$ (sodium sulfite) to give a compound of the formula V which is then converted by reduction of the nitro group into the corresponding aniline. A compound of the formula I is finally obtained by heating this aniline of the compound of the formula V.

The invention also relates to a pharmaceutical composition or medicament which comprises at least one of the compounds of the formula I and/or its physiologically acceptable salts and/or their prodrugs and, if appropriate, additional excipients.

The compounds of the formula I, and/or their physiologically acceptable salts and/or their prodrugs can be used for preparing medicaments.

Such medicaments are suitable, in particular, for treating type 1 and 2 diabetes, insulin resistance and pathological obesity. In addition, they are also suitable for treating elevated blood lipid levels, hypertension, atherosclerosis, immune system dysfunctions, autoimmune diseases, allergic diseases such as asthma, osteoporosis, disturbed proliferation, such as cancer and psoriasis, diseases where the production of growth factors, hormones or cytokines which effect the release of growth hormones is reduced or increased, infectious diseases or disorders of the nervous system, such as Alzheimer's disease and schizophrenia.

The compounds of the formula I, and/or their physiologically acceptable salts and/or their prodrugs can furthermore be used for preparing a medicament which inhibits a PTPase. Suitable PTPases are, in particular, PTP1B, CD45, LAR, SHP-1, SHP-2, PTPa or HePTP.

Finally, compounds of the formula I and/or their physiologically acceptable salts and/or their prodrugs can be used for preparing a medicament for the treatment of diseases, in particular, type 1 and 2 diabetes, insulin resistance, pathological obesity, elevated blood lipid levels, hypertension, atherosclerosis, immune system dysfunctions, autoimmune diseases, allergic diseases such as asthma, osteoporosis, disturbed proliferation, such as cancer and psoriasis, diseases where the production of growth factors, hormones or cytokines which effect the release of growth hormones is reduced or increased, disorders of the nervous system such as Alzheimer's disease and schizophrenia and infectious diseases.

The invention relates to the preparation of a medicament comprising at least one compound of this invention, which comprises mixing the active compound with a pharmaceutically acceptable excipient, and bringing this mixture into a form suitable for administration.

List of Abbreviations:
aa amino acids
DBU 1,5-diazabicyclo(4.3.0)non-5-ene
DMSO dimethyl sulfoxide
DTT dithiotreitol
EDTA ethylenediaminetetraacetic acid
EtOAc ethyl
EGTA ethylenebis(oxyethylenenitrilo)tetraacetic acid
h hour
HPLC high pressure liquid chromatography
MeOH methanol
MOI multiplicity of infection
MS mass spectroscopy
NMR nuclear magnetic resonance
PAGE polyacrylamide gel electrophoresis
RP reversed phase
RT room temperature
SDS sodium dodecylsulfate
TFA trifluoroacetic acid The present invention, thus generally described, will be understood more readily by reference to the examples listed below, which serve to illustrate the present invention without limiting it.

EXAMPLES

TABLE 1 formula I

| Compound | R1 | R2 | R3 | X | Y |
|---|---|---|---|---|---|
| 1 | 7-H | 6-H | 5-H | N | N |
| 2 | 7-H | 6-H | 5-$CH_3$ | N | O |
| 3 | 7-H | 6-H | 5-H | O | N |
| 4 | In positions 4 and 5, in each case two radicals R1 and R2 or R2 and R3 or R1 and R3 together form a fused benzene radical; the respective remaining radical located in position 7 or 6 is H | | | O | N |
| 5 | 7-H | 6-$NO_2$ | 5-H | O | N |
| 6 | 7-H | 6-$NH_2$ | 5-H | O | N |
| 7 | 7-H | 6-H | 5-COO($CH_3$) | O | N |
| 8 | 7-H | 6-H | 5-COOH | O | N |
| 9 | 7-H | 6-H | 5-CON ($CH_2$—$CH_2$-phenyl-3,4-O—$CH_2$-phenyl) | O | N |
| 10 | 7-H | 6-H | 5-CON ($CH_2$-phenyl-4-O—$(CH_2)_7$—$CH_3$) | O | N |
| 11 | 7-H | 6-H | 5-CON (($CH_2)_{15}$—$CH_3$) | O | N |
| 12 | 7-H | 6-H | 5-COO($CH_3$) | N | O |
| 13 | 7-H | 6-H | 5-COOH | N | O |
| 14 | 7-H | 6-H | 5-CON ($CH_2$—$CH_2$-phenyl-3,4-O—$CH_2$-phenyl) | N | O |
| 15 | 7-H | 6-H | 5-CON ($CH_2$-benzimidazolyl-2,5-S-phenyl) | N | O |

Inhibitors of phosphatases are described, inter alia, in WO97/3974 (cinnamic acid derivatives as inhibitors of PTP) which is hereby incorporated herein by reference. Unspecific phosphatase inhibition by vanadium oxo complexes and other vanadium complexes results in improved insulin resistance.

Enzymatic test systems for detecting phosphatase inhibition
In an in vitro assay, the compounds of the formula I were tested for their phosphatase-inhibiting action. Enzyme preparation and assay were carried out as follows.
Obtaining the Enzyme Preparation:
A) Cell Culture:
Sf9 cells (=*Spodoptera frugiperda* cell type; obtainable from Invitrogen) are cultivated in spinner flasks at 28° C. in Grace's supplemented medium (Gibco-BRL) with 10% heat-inactivated fetal calf serum (Gibco-BRL) according to the protocol of Summers and Smith (A Manual for Methods for Baculovirus Vectors and Insect Culture Procedures [Bulletin No. 15555]. Texas A & M University, Texas Agricultural Experiment Station, College Station, Tex., 1987). Construction of recombinant Baculovirus transfer vectors: cDNA encoding the regulatory and catalytic domains of human PTP1B, but without the carboxy-terminal hydrophobic region (corresponding to 1–299 aa) was obtained via polymerase chain reaction using primers with added donation sites and suitable cDNA matrices (obtainable, for example, from Invitrogen) and then cloned in Baculovirus expression vectors (Amersham Pharmacia Biotech.). The recombinant Baculoviruses were prepared using the Bac-to-Bac Baculovirus expression system (obtainable from Gibco-BRL). The gene was cloned into the pFASTBAC donor plasmid (obtainable from Life Technologies). The resulting plasmid was transformed into competent DH10BAC *Escherichia coli* cells (obtainable from Life Technologies). Following transposition and antibiotic selection, the recombinant plasmid DNA of selected *E. coli* colonies was isolated and then used for the transfection of Sf9 insect cells. The virus particle in the supernatant medium was amplified three times, up to a viral stock volume of 500 ml.

B) Production of Recombinant Protein:

Baculovirus infection of a 500 ml spinner culture of Sf9 cells was carried out essentially as described by Summers and Smith (see above). At a density of $1-3 \times 10^6$ cells/ml, Sf9 cells were pelleted by centrifugation at 300 g for 5 min, the supernatant was removed and the cells were resuspended at a density of $1 \times 10^7$ cell/ml in a suitable recombinant viral stock (MOI 10). The culture was shaken carefully at room temperature for 1.5 h and fresh medium was then added to a cell density of $1 \times 10^6$ cells/mi. The cells were then cultivated in suspension at 28° C. for suitable periods following postinfection.

C) Cellular Fractionation and Total Cell Extracts of Infected Sf9 Cells:

Following postinfection, aliquots were subjected to an analysis of protein expression by SDS-PAGE and Western blot analysis. Cellular fractionation was carried out as described (Cromlish, W. and Kennedy, B. Biochem. Pharmacol. 52: 1777–1785, 1996). Total cell extracts were obtained of 1 ml aliquots of the infected Sf9 cells after certain intervals postinfection. The pelleted cells (300 xg, 5 min) were washed once in phosphate-buffered saline (4° C.), resuspended in 50 μl of water and broken up by repeated freezing/thawing. Protein concentrations were determined using the Bradford method, with bovine serum albumin as standard.

Assay:

A) Dephosphorylation of a Phosphopeptide:

This assay is based on the release of phosphate from a consensus substrate peptide which is detected in the nanomolar concentration range by the Malachite Green/ammonium molybdate method (Lanzetta, P. A., Alvarez, L. J., Reinach, P. S., Candia, O. A. Anal Biochem. 100: 95–97, 1979) adapted for the microtiter plate format. The dodecatrisphosphopeptide, TRDIYETDYYRK (Biotrend, Cologne) corresponds to the amino acids 1142–1153 of the catalytic domain of the insulin receptor and is (auto) phosphorylated on the tyrosine residues 1146, 1150, and 1151. The recombinant hPTP1B was diluted with assay buffer (40 mM Tris/HCl, pH 7.4, 1 mM EDTA, 20 mM DTT), corresponding to an activity of 1000–1500 nmol/min/mg of protein, and then preincubated (a 20 μl portion, 15 min, 30° C.) in the absence or presence of the test substance (5 μl) in the desired concentration (final concentration DMSO 2% max.) in a total volume of 90 μl (assay buffer). To initiate the dephosphorylation reaction, the peptide substrate (10 μl, pre-warmed to 30° C.) was added to the preincubated enzyme preparation with or without test substance (final concentration 0.2–200 μM), and the incubation was continued for 1 h. The reaction was terminated by addition of 100 μl of Malachite Green hydrochloride (0.45%, 3 parts), ammonium molybdate tetrahydrate (4.2% in 4 N HCl, 1 part) and 0.5% of Tween 20 as stop solution. Following 30 min of incubation at 22° C. for color development, the absorption at 650 nm was determined using a microtiter plate reader (Molecular Devices). Samples and blank values were determined in three replications. The PTP1B activity was calculated as nanomoles of released phosphate per min and mg of protein using potassium phosphate as standard. The inhibition of recombinant hPTP1B by test substances was calculated as a percentage of the phosphatase control. The $IC_{50}$ values show significant correlation with a four-parameter nonlinear logistic regression curve.

B) Cleavage of P-nitrophenyl Phosphate:

This assay is based on the change in absorption of the non-physiological substrate p-nitrophenyl phosphate during cleavage to nitrophenol under standard conditions (Tonks, N. K., Diltz, C. D:, Fischer, E. H. J. Biol. Chem. 263: 6731–6737, 1988; Burke T. R., Ye, B., Yan, X. J., Wang, S. M., Jia, Z. C., Chen, L., Zhang, Z. Y., Barford, D. Biochemistry 35: 15989–15996, 1996). The inhibitors, at a suitable dilution, are pipetted to the reaction mixtures containing 0.5–5 mM of p-nitrophenyl phosphate. The following buffers were used (total volume 100 μl): (a) 100 mM sodium acetate (pH 5.5), 50 mM NaCl, 0.1% (w/v) bovine serum albumin, 5 mM glutathione, 5 mM DTT, 0.4 mM EGTA and 1 mM EDTA; (b) 50 mM Hepes/KOH (pH 7.4), 100 mM NaCl, 0.1% (w/v) bovine serum albumin, 5 mM glutathione, 5 mM DTT and 1 mM EDTA. The reaction was started by addition of enzyme and carried out in microtiter plates at 25° C. for 1 h. The reaction was terminated by addition of 100 pi of 0.2 N NaOH. The enzyme activity was determined by measuring the absorption at 405 nm, with suitable corrections for the absorption of the test substances and of p-nitrophenyl phosphate. The results were expressed in percent of the control by comparing the amount of p-nitrophenol formed in the samples treated with test substance (nmol/min/mg of protein) with the amount in the untreated samples. Mean values and standard deviations were calculated and the IC50 values were determined by regression analysis of the linear portion of the inhibition curves.

The test results show that the compounds of the formula I according to the invention have an inhibitory effect on the phosphotyrosine phosphatase 1B (PTP1 B). It is known that PTP1B plays an important role in intracellular signal cascades. The compounds are therefore suitable for treating in particular, type 1 and 2 diabetes, insulin resistance and pathological obesity. Owing to the fact that they inhibit PTP1B, the compounds are also suitable for treating hyperglycemia, hypertension, atherosclerosis, immune system dysfunctions, autoimmune diseases, allergic diseases such as asthma, osteoporosis, proliferation disturbances, such as cancer and psoriasis, diseases with reduced or increased production of growth factors, hormones or cytokines which effect the release of growth hormones, disorders of the nervous system, such as Alzheimer's disease and schizophrenia, and infectious diseases.

Preparation of exemplary compounds (numeration according to table 1): Below, the preparation of some compounds is described in detail; the other compounds of the formula I were obtained in a similar manner:

Compound 1: 1,3-Dihydrobenzo[1,2,5]thiadiazole 2,2-dioxide

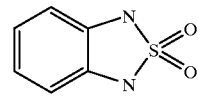

A solution of 1,2-phenylenediamine (91 mg, 0.84 mmol) and sulfamide (81 mg, 0.84 mmol) in diglyme (2.5 ml) is stirred at 155° C. for 1.5 h. After cooling to RT, the reaction solution is poured into ice-water (15 ml) and the product is extracted with ethyl acetate. The solvent is distilled off under reduced pressure and the red residue is purified by flash chromatography (1:1 ethyl acetate/toluene).

Yield: 41 mg (35%).

$^1$H-NMR (D$_6$-DMSO): δ10.8 (s, 2 H, NH), 6.88 (m, 2H) aryl, 6.8 (m, 2 H) aryl.

MS (ESI-MS) 171.1 (M+1).

Compound 2: 6-Methyl-3H-benzo[1,2,3]oxathiazole 2,2-dioxide

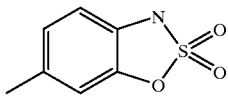

N-(2-Hydroxy-4-methylphenyl)-4-methylbenzenesulfonamide Pyridine (810 μl) and then, a little at a time, p-toluenesulfonyl chloride (1.91 g, 10 mmol) are added to a solution of 2-amino-5-methylphenol (1.23 g, 10 mmol) in CH$_2$Cl$_2$ (20 ml). The reaction mixture is stirred at 40° C. for 4 h. The solvent is distilled off under reduced pressure, ethyl acetate is added to the residue and the solid is filtered off with suction.

Yield: 2.32 g (83%)

6-Methyl-3-(toluene-4-sulfonyl)-3H-benzo[1,2,3]oxathiazole 2,2-dioxide At-78° C., a solution of sulfuryl chloride (450 μl, 5.41 mmol) in CH$_2$Cl$_2$ (10 ml) is slowly added dropwise to a solution of N-(2-hydroxy-4-methylphenyl)-4-methyl-benzenesulfonamide (1.5 g, 5.41 mmol) and triethylamine (1.5 ml), and the mixture is stirred at −78° C. for one hour. After thawing to RT, the solvent is distilled off under reduced pressure and the residue is purified by RP chromatography.

Yield: 592 mg (32%).

6-Methyl-3H-benzo[1,2,3]oxathiazole 2,2-dioxide
6-Methyl-3-(toluene-4-sulfonyl)-3H-benzo[1,2,3]oxathiazole 2,2-dioxide (100 mg, 0.295 mmol) is dissolved in acetonitrile (5 ml). A solution of sodium azide (of 20 mg, 0.29 mmol of sodium azide in 1 ml of H$_2$O) is added to this solution, and the mixture is stirred at RT overnight. The mixture is then stirred at 60° C. for 1 h, the solvent is distilled off under reduced pressure and the residue is purified by RP chromatography.

Yield: 47 mg (85%).

$^1$H-NMR (D$_6$-DMSO): δ 6.51 (d, 1 H, aryl), 6.45 (d, 1 H, aryl), 6.29 (m, 1 H, aryl), 2.14 (s, 3 H, CH$_3$).

MS (ESI-MS, ES-) 184.9 (M−1).

Compound 3: 5-Methyl-3H-benzo[1,2,3]oxathiazole 2,2-dioxide

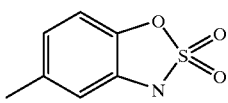

5-Methyl-3H-benzo[1,2,3]oxathiazole 2,2-dioxide was synthesized starting with 2-amino-4-methylphenol, according to the sequence described under example 2. $^1$H-NMR (D$_6$-DMSO): δ 6.53 (d, 1 H, aryl), 6.23 (m, 1 H, aryl), 6.10 (dd, 1 H, aryl), 2.13 (s, 3 H, CH$_3$).

MS (ESI-MS, ES-) 184.9 (M−1).

Compound 4: 1 H-3-Oxa-2-thia-1-azacyclopenta[a]naphthyl 2,2-dioxide

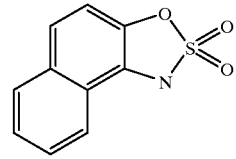

1 H-3-Oxa-2-thia-1-azacyclopenta[a]naphthyl 2,2-dioxide was synthesized from 1-aminonaphthyl-2-ol, according to the sequence described under example 2. $^1$H-NMR (D$_6$-DMSO): δ 7.8 (dd, 1 H, aryl), 7.66 (dd, 1 H, aryl), 7.23 (m, 2 H, aryl), 7.1 (d, I H aryl), 6.9 (d, 1 H, aryl). MS (ESI-MS, ES-) 221 (M−1).

Compound 5: 6-Nitro-3H-benzo[1,2,3]oxathiazole 2,2-dioxide

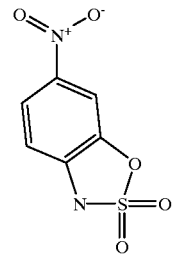

A solution of 2-amino-5-n nitrophenol (7.7 g, 50 mmol) in acetonitrile (300 ml) is treated with N-ethyldiisopropylamine (18.7 ml, 110 mmol) and N, N'-sulfuryldiimidazole (10.8 g, 55 mmol) and boiled at reflux for 18 h. After cooling to RT, the solvent is distilled off under reduced pressure, the residue is taken up in 1 N HCl and the product is extracted with ethyl acetate. The product is then purified by flash chromatography (17:2:1, EtOAc/MeOH/H$_2$O).

Yield: 8.3 g (76.9%).

$^1$H-NMR (D$_6$-DMSO): δ 7.6 (dd, 1 H, aryl), 7.58 (s, 1 H, aryl), 6.55 (d, 1 H, aryl).

MS (ESI-MS, ES-) 214.9 (M−1).

Compound 6: 6-Amino-3H-benzo[1,2,3]oxathiazole 2,2-dioxide

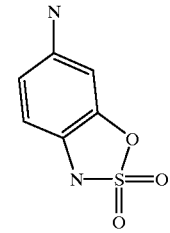

A solution of 6-nitro-3H-benzo[1,2,3]oxathiazole 2,2-dioxide (example 5) (8.1 g, 37 mmol) in methanol (250 ml)

is hydrogenated at atmospheric pressure in the presence of Pd-C. The catalyst is then filtered off, the clear solution is treated with methanolic HCl (1 N) and the solvent is distilled off under reduced pressure. The residue is dissolved in ethanol and the product crystallizes after addition of diethyl ether.
Yield: 3.95 g (57.3%).
Compound 7: Methyl 2,2-dioxo-2,3-dihydro-2,6-benzo[1,2,3]oxathiazole-5-carboxylate

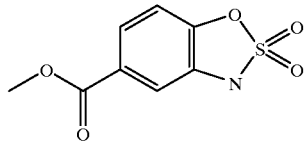

3 g of methyl 3-amino-4-hydroxybenzoate (0.018 mol), 3.9 g of sulfonyldiimidazole (0.02 mol) and 3 g of DBU (0.02 mol) are dissolved in 50 ml of acetonitrile and the solution is degassed and then heated at boiling point for 3h.
For work-up, the solution is diluted with 120 ml of ethyl acetate and extracted with 50 ml of 1 N HCl. The organic phase is dried over magnesium sulfate and the solvent is distilled off under reduced pressure.
The crude product is used without purification for the next step.
Yield: 3.6 g (88%)
$^1$H-NMR (D6-DMSO): δ 7.55 (dd, 1 H, aromat.), 7.45 (d, 1 H, aromat.), 7.23 (d, 1 H, aromat.), 3.85 (s, 3H, OMe). MS (ESI-MS) 230.1 (M+1).
Compound 8: 2,2-Dioxo-2,3-dihydro-2,6-benzo[1,2,3]oxathiazole-5-carboxylic acid

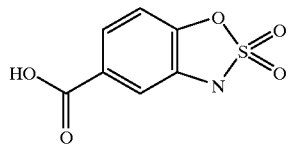

3.3 g of compound 1 (21 mmol) are dissolved in a solution of 1.25 g of NaOH in 70 ml of water. The reaction mixture is stirred at 25° C. for 4 h.

The mixture is then acidified to pH 2 using 2N HCl and evaporated to dryness. To remove the NaCl, the residue is taken up in 150 ml of acetone and filtered, and the solvent is distilled off. The crude product is used without purification for the next step.

Yield: 2.3 g (75%)

$^1$H-NMR (D6-DMSO): δ 7.54 (dd, 1 H, aromat.), 7.40 (d, 1 H, aromat.), 7.27 (d, 1 H, aromat.). MS (ESI-MS) 216.1 (M+1).

Compound 9: N-[2-(3,4-Bisbenzyloxyphenyl)ethyl]-2,2-dioxo-2,3-dihydro-2,6-benzo[1,2,3]oxathiazole-5-carboxamide

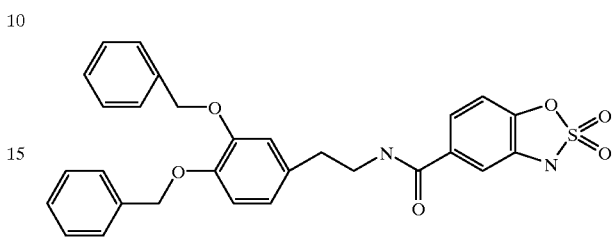

A solution of 100 mg of compound 3 (0.46 mmol), 160 mg of 2-(3,4-bisbenzyloxyphenyl)ethylamine hydrochloride (0.6 mmol), 115 mg of EDC (0.6 mmol), 81 mg of HOBT and 260 mg of ethyldiisopropylamine in 2 ml of DMF is stirred at 25° C. for 5 h.

The mixture is then diluted with 20 ml of ethyl acetate and extracted with 10 ml of 2N HCl. The organic phase is dried over magnesium sulfate and the solvent is distilled off. The crude product is purified by HPLC (RP18, acetonitrile/water 0.1% TFA).

Yield: 66 mg (40%).

$^1$H-NMR (D6-DMSO): δ 8.49 (t, 1H, NH), 7.46–7.23 (m, 13 H, aromat.), 6.97 (d, 2 H, aromat.), 6.74 (dd, 1 H, aromat.), 5.08 (s, 4H, OCH$_2$), 3.43 (dt, 2H, NCH$_2$), 2.74 (2H, t, CH$_2$). MS (ESI-MS) 531.2 (M+1).

Compound 10: N-(4-Octyloxybenzyl)-2,2-dioxo-2,3-dihydro-2,6-benzo[1,2,3]oxathiazole-5-carboxamide 4

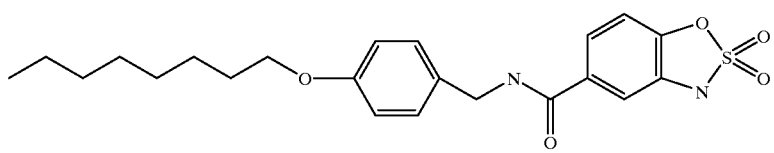

Compound 4 is prepared as described for compound 3.

Yield: 63 mg (52%)

$^1$H-NMR (D6-DMSO): δ 8.95 (t,1 H, NH), 7.52 (dd, 1 H, aromat.), 7.45 (d, 1 H, aromat.), 7.3 (d, 1 H, aromat.), 7.22 (d, 2 H, aromat.), 6.86 (d, 2 H, aromat.), 4.37 (d, 2H, NCH$_2$), 3.91 (t, 2H, OCH$_2$), 1.65 (m, 2H, CH$_2$), 1.45–1.2 (m, 10H, CH$_2$), 0.86 (t, 3H, CH$_3$). MS (ESI-MS) 433.2 (M+1).

Compound 11: N-Hexadecyl-2,2-dioxo-2,3-dihydro-2,6-benzo[1,2,3]oxathiazole-5-carboxamide 5

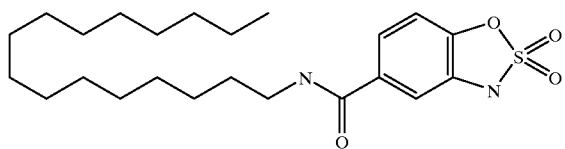

Compound 5 is prepared as described for compound 3.
Yield: 51 mg (26%)
$^1$H-NMR (D6-DMSO): δ 8.35 (t, 1H, NH), 7.38 (d, 1 H, aromat.), 7.34 (s, 1 H, aromat.), 7.2 (d, 1 H, aromat.), 3.21 (dt, 2H, NCH$_2$), 1.5 (m, 2H, CH$_2$),1.4 (m, 26H, CH$_2$), 0.85 (t, 3H, CH$_3$). MS (ESI-MS) 439.3 (M+1).

Compound 12: Methyl 2,2-dioxo-2,3-dihydro-2,6-benzo[1,2,3]oxathiazole-6-carboxylate 6

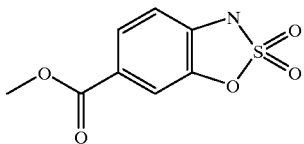

Compound 6 is prepared as described for compound 1.
Yield: 3.35 g (82%)
$^1$H-NMR (D6-DMSO): δ 7.43 (dd, 1 H, aromat.), 7.19 (d, 1 H, aromat.), 6.53 (d, 1 H, aromat.). MS (ESI-MS) 227.9 (M−1). Compound 13: 2 ,2-Dioxo-2,3-dihydro-2,6-benzo[1,2,3]oxathiazole-6-carboxylic acid 7

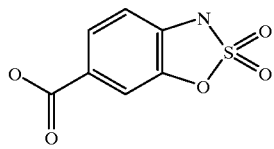

Compound 7 is prepared from 6 as described for compound 2.
Yield: 2.2 g (71%)
$^1$H-NMR (D6-DMSO): δ 7.46 (dd, 1 H, aromat.), 7.25 (d, 1 H, aromat.), 6.46 (d, 1 H, aromat.) 3.73 (s, 3H, Ome). MS (ESI-MS) 213.9 (M−1).

Compound 14: N-[2-(3,4-Bisbenzyloxyphenyl)ethyl]-2,2-dioxo-2,3-dihydro-2,6-benzo[1,2,3]oxathiazole-6-carboxamide 8

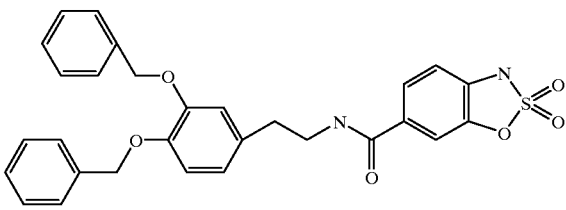

Compound 8 is prepared from 7 as described for compound 3.
Yield: 4,1 g (25%)
$^1$H-NMR (D6-DMSO): δ 8.33 (t, 1H, NH), 7.55 (m, 2 H, aromat.), 7.45–7.3 (m, 10 H, aromat.), 6.96 (d, 2 H, aromat.), 6.86 (d, 1 H, aromat.), 6.74 (dd, 1 H, aromat.), 5.08 (s, 4H, OCH$_2$), 3.41 (dt, 2H, NCH$_2$), 2.73 (2H, t, CH$_2$). MS (ESI-MS) 531.3 (M+1).

Compound 15: N-(5-Phenylsulfanyl-1H-benzoimidazol-2-ylmethyl)-2,2-dioxo-2,3-dihydro-2,6-benzo[1,2,3]oxathiazole-6-carboxamide 9

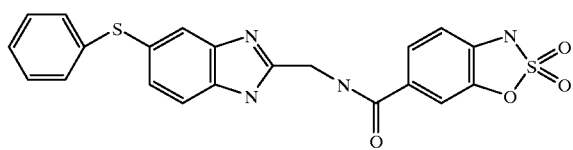

Compound 9 is prepared from 7 as described for compound 3
Yield: 6,9 g (34%)
$^1$ H-NMR (D6-DMSO): δ 8.96 (t, 1H, NH), 7.75 (d, 1 H, aromat.), 7.61 (d, 1 H, aromat.), 7.46, (m, 2H, aromat.) 7.41–7.3 (m, 6 H, aromat.), 6.55 (d, 1 H, aromat.), 4.81 (d, 2H, NCH$_2$). MS (ESI-MS) 453.2 (M+1).

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

As used herein and in the following claims, articles such as "the", "a" and "an" can connote the singular or the plural.

All documents referred to herein are specifically incorporated herein by reference in their entireties.

We claim:
1. A compound of the formula I

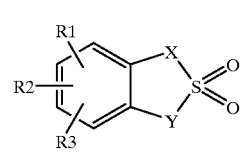

in which
X is CH$_2$;
Y is CH$_2$;
R1, R2, R3 are each independently of one another
  NH$_2$, COOH;
  CONH$_2$, CONH(C$_1$–C$_{16}$)alkyl, CONH(C$_1$–C$_{16}$) alkenyl, CONH(C$_1$–C$_6$)alkyl-phenyl, where phenyl may be mono- to trisubstituted by O-(C$_1$–C$_{10}$)alkyl or O-(C$_1$–C$_{10}$)alkyl-phenyl, CONH(C$_1$–C$_6$)alkyl-benzimidazole, where the benzimidazole ring may be mono- to trisubstituted by S-phenyl, wherein the S-phenyl may be mono- to trisubstituted by F, Cl, Br, I, OH, CF$_3$, NO$_2$, CN, OCF$_3$, O-(C$_1$–C$_{10}$)alkyl, NH$_2$, NH(C$_1$–C$_6$)alkyl, COOH, COO(C$_1$–C$_6$)alkyl, CONH$_2$;
  (C$_2$–C$_6$)alkynyl, (C$_1$–C$_6$)alkyl-COOH, (C$_1$–C$_6$)alkyl-aryl, where aryl may be phenyl, naphthyl, biphenyl, thienyl or pyridyl and the aryl moiety may in each case be mono- to trisubstituted by F, Cl, Br, I, OH, CF$_3$, NO$_2$, CN, OCF$_3$, O-(C$_1$–C$_{10}$)alkyl, NH$_2$, NH(C$_1$–C$_6$)alkyl, COOH, COO(C$_1$–C$_6$)alkyl, CONH$_2$; biphenyl, 1- or 2-naphthyl, 2-,3- or 4-pyridyl, 2- or 3-furanyl or 2- or 3-thienyl, where the phenyl, biphenyl, naphthyl, pyridyl, furanyl or thienyl rings may in each case be mono- to trisubstituted by F, Cl, Br, I, OH, CF$_3$, NO$_2$, CN, OCF$_3$, O-($C_1$–$C_{10}$)alkyl, $NH_2$, NH($C_1$–$C_6$)alkyl, COOH, COO($C_1$–$C_6$)alkyl, $CONH_2$; ($C_3$–$C_{18}$)cycloalkyl, where in the alkyl radicals one or more hydrogens may be replaced by fluorine or one hydrogen may be replaced by OH, ($C_1$–$C_6$)alkyl-phenyl or O-($C_1$–$C_6$)alkyl-phenyl, NCO, $NSO_3$-($C_1$–$C_{10}$)alkyl; or in each case two of the radicals R1 and R2 or R2 and R3 or R1 and R3 together form a fused aryl radical, where aryl may be phenyl, naphthyl, biphenyl, thienyl or pyridyl and the aryl moiety may in each case be mono- to trisubstituted by F, Cl, Br, I, OH, $CF_3$, $NO_2$, CN, $OCF_3$, O-($C_1$–$C_{10}$)alkyl, $NH_2$, NH($C_1$–$C_6$)alkyl, COOH, COO($C_1$–$C_6$)alkyl, $CONH_2$;

or its physiologically acceptable salts.

2. A pharmaceutical composition comprising an effective amount of at least one compound as claimed in claim 1 and a pharmaceutically acceptable excipient.

3. A method of preparing a pharmaceutical composition comprising the steps of mixing one or more compounds of claim 1 with one or more pharmaceutically acceptable excipients and bringing this mixture into a form suitable for administration.

* * * * *